(12) United States Patent
Gertner

(10) Patent No.: US 7,712,470 B2
(45) Date of Patent: May 11, 2010

(54) DEVICES WITH INTEGRAL MAGNETS AND USES THEREOF

(75) Inventor: Michael Gertner, 520 Laurel St., Menlo Park, CA (US) 94025

(73) Assignee: Michael Gertner, Menlo Park, CA (US)

( * ) Notice: Subject to any disclaimer, the term of this patent is extended or adjusted under 35 U.S.C. 154(b) by 1001 days.

(21) Appl. No.: 11/424,226

(22) Filed: Jun. 14, 2006

(65) Prior Publication Data

US 2008/0140100 A1 Jun. 12, 2008

Related U.S. Application Data

(60) Provisional application No. 60/691,050, filed on Jun. 16, 2005.

(51) Int. Cl.
*A61B 19/00* (2006.01)
(52) U.S. Cl. ..................................................... 128/899
(58) Field of Classification Search ................ 128/899; 600/9, 12, 13, 424; 604/270, 95.01, 95.05
See application file for complete search history.

(56) References Cited

U.S. PATENT DOCUMENTS

| | | | | | |
|---|---|---|---|---|---|
| 4,054,128 | A | * | 10/1977 | Seufert et al. | 600/116 |
| 5,681,260 | A | * | 10/1997 | Ueda et al. | 600/114 |
| 6,126,647 | A | * | 10/2000 | Posey et al. | 604/270 |
| 6,772,001 | B2 | * | 8/2004 | Maschke | 600/423 |

* cited by examiner

*Primary Examiner*—Samuel G Gilbert

(57) ABSTRACT

In one embodiment, an elongate body with a proximal end and a distal end is disclosed and which is controllable by an operator at the proximal end; in one embodiment, the elongate body is a catheter and the catheter tip is located at the distal end. The body contains numerous magnets along its length, at least one of which is an electromagnet, controllable by means of a current delivered by the operator of the body at the proximal end of the body. The magnets are placed such that a force is created at the distal end of the elongate body. The magnetic forces which control the distal end of the body originate from the controllable magnets placed on the body.

18 Claims, 5 Drawing Sheets

DEVICES WITH INTEGRAL MAGNETS AND USES THEREOF

PRIORITY DATA

This application claims priority to provisional application Ser. No. 60/691,050 filed Jun 16, 2005 titled Intracorporeal devices with integral magnets and uses thereof filed by Michael Gertner.

SUMMARY OF INVENTION

Disclosed in this invention is an elongate body with a proximal end and a distal end and which is controllable by an operator at the proximal end; in one embodiment, the elongate body is a catheter and the catheter tip is located at the distal end. The body contains numerous magnets along its length, at least one of which is an electromagnet, controllable by means of a current delivered by the operator of the body at the proximal end of the body. The magnets are placed such that a force is created at the distal end of the elongate body. The magnetic forces which control the distal end of the body originate from the controllable magnets placed on the body.

In some embodiments, the elongate body is a catheter for navigation within a patient. Torque is applied by the magnets on the body to the distal end for purposes of navigation within a patient. In some embodiments, the magnets apply force to the distal end of the elongate body for purposes of applying a cyclic force to tissue. In some embodiments, the magnets are used to impart kinetic energy to particles. In some embodiments, the magnets are used to create a pressure head in a fluid in the catheter.

DETAILED DESCRIPTION OF THE INVENTION

Figure 1A:
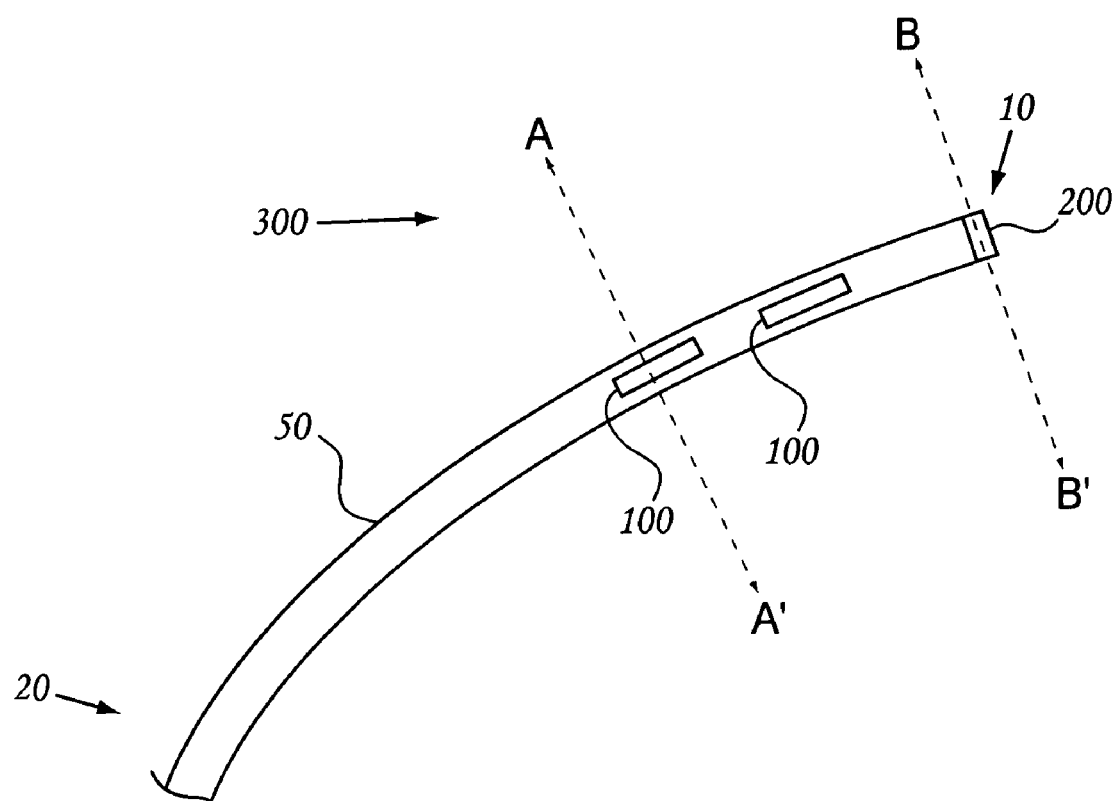
FIG. 1a depicts the distal end of an elongate body incorporating at least one electromagnet.
Figure 1B:
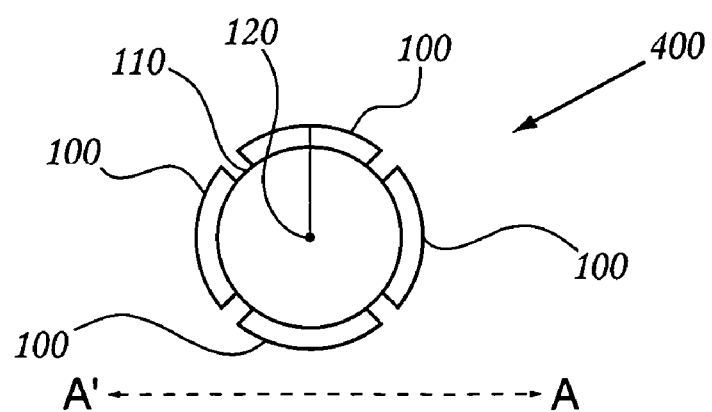
FIG. 1b depicts a cross section along the device in FIG. 1a and depicts the distance of the magnets from the longitudinal center of the elongate body.

FIG. 1a depicts an elongate body 50 with a distal end 10 and a proximal end 20. On the elongate body 50 is at least one magnet 100 and one magnetic or paramagnetic material 200 at the distal end 10. Magnet 100 and can be a permanent magnet or an electromagnet. FIG. 1b depicts a cross-section at region A-A' 400. Magnets 100 are elevated from the surface 110 of the elongate body 50 and are placed a distance 120 from the center of the cross-section. The magnets 100 can be any length, from less than one mm to greater than one centimeter. Magnets 100 can be placed anywhere along the length of elongate body depending on the desired functionality of the magnets on the elongate body. Magnets 100 can also cover any circumference of the elongate body.

The elongate body 50, in some embodiments, can be a catheter that is placed inside the a patient. The distal end of the elongate body can be adapted to be placed through a sheath and into the blood vessels of a patient. Alternatively, the elongate body can be adapted to be placed into the interstitial substance of a patient, such as, for example, to reach a tumor in the lung or to reach a deteriorating spinal disc, for example.

The controlled magnetic field or fields which originate on the body allow for desired functionality of the elongate body 50, e.g. through manipulation of the distal end 10 of the body or (as described below) manipulation of actuators or particles on or in the elongate body. As an example, the direction of the elongate body can be controlled by activating the one or more magnets or electromagnets. Electromagnets are controlled or activated by current whereas permanent magnets can be controlled through magnetic shielding, which when removed, allows the permanent magnets to interact with one another or with the electromagnets. Both activation with current and removal of shielding are included in the term "activation."

Figure 1C:
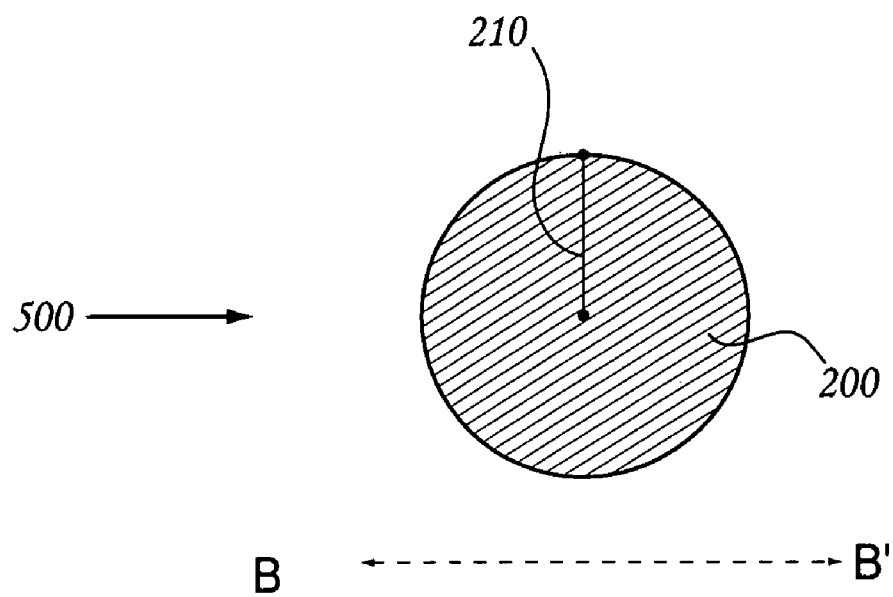
FIGS. 1c-d depict different configurations of the distal end of the elongate body.
Figure 1D:
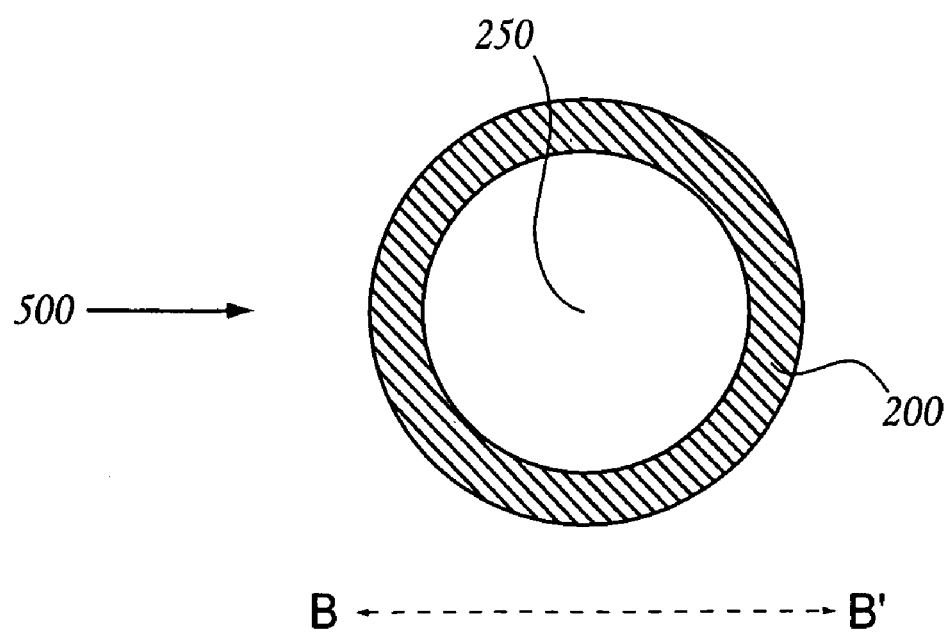

FIG. 1C depicts cross-section B-B' at the distal end 10 of the elongate body 50. A magnetic or paramagnetic material 200 is contained at distal end 10. Although the material 200 is depicted as filling the cross-section of the catheter B-B', the material 200 does not have to fill the entire cross-section and may fill only a 5-10%, 10%-50%, or a 50%-99% portion of the cross-section. Material 200 can form an annulus with a lumen 250 which is within the elongate body 50, as depicted in FIG. 1D.

The distance 120 of magnets 100 from the center axis of the elongate body at its cross-section is greater than the distance of material 200 from the center 210 of the elongate body at its respective cross-section; therefore when magnet 100 is induced to attract or repel material 200 (see below), a torque T is created on the distal end of the elongate body. The torque T on the distal end of the elongate body, in turn, can induce a bend in the elongate body and can therefore be used for navigation purposes within the body of a patient (e.g. within the vascular system).

Elongate body 50 can be made from one or more of or any type of biocompatible material typically used in devices that enter blood vessels or other tissues; materials include polyurethane, silicone, or nitinol. In one embodiment, elongate body is made from a shape memory alloy such as nitinol so that after torque is applied to the body tip, the catheter and tip return to a neutral, in-line position.

Figure 2:
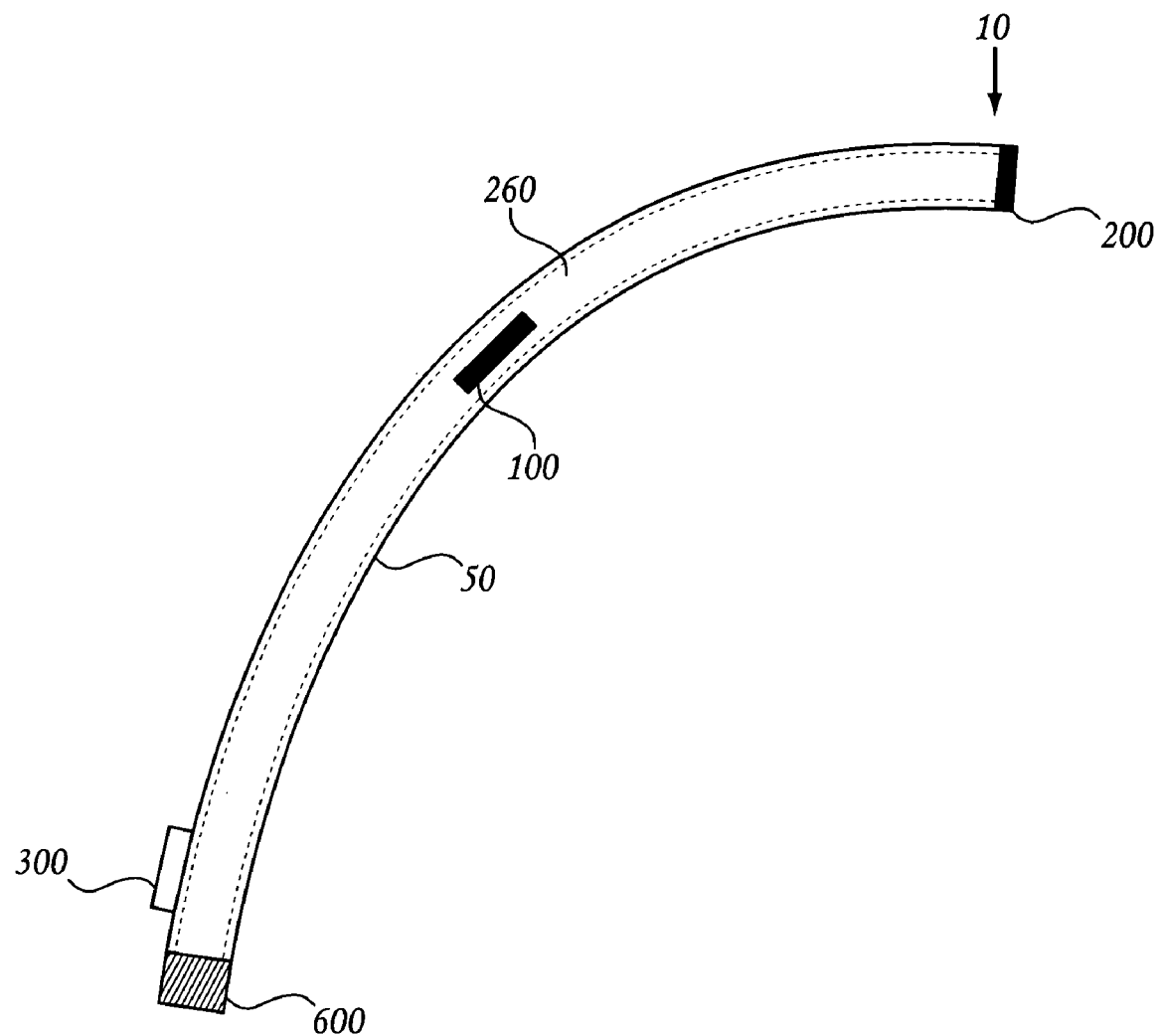
FIG. 2 depicts the proximal end of the elongate body and a control system at the proximal end.

FIG. 2 depicts elongate body 50 and a user interface end 600 of the elongate body. Control circuitry 300 is integral to the user interface end 600 of the elongate body 50. Circuitry 300 controls power delivery to magnets 100 via electrical connections 260.

Circuitry 300 integrates user inputs (e.g. a physician applying directional forces to a joystick) and sends proper signals to the electromagnet(s) 100 to enable actuation of the distal tip 10. Actuation of different electromagnets enables varying directionality or functionality of the tip.

Figure 3A:
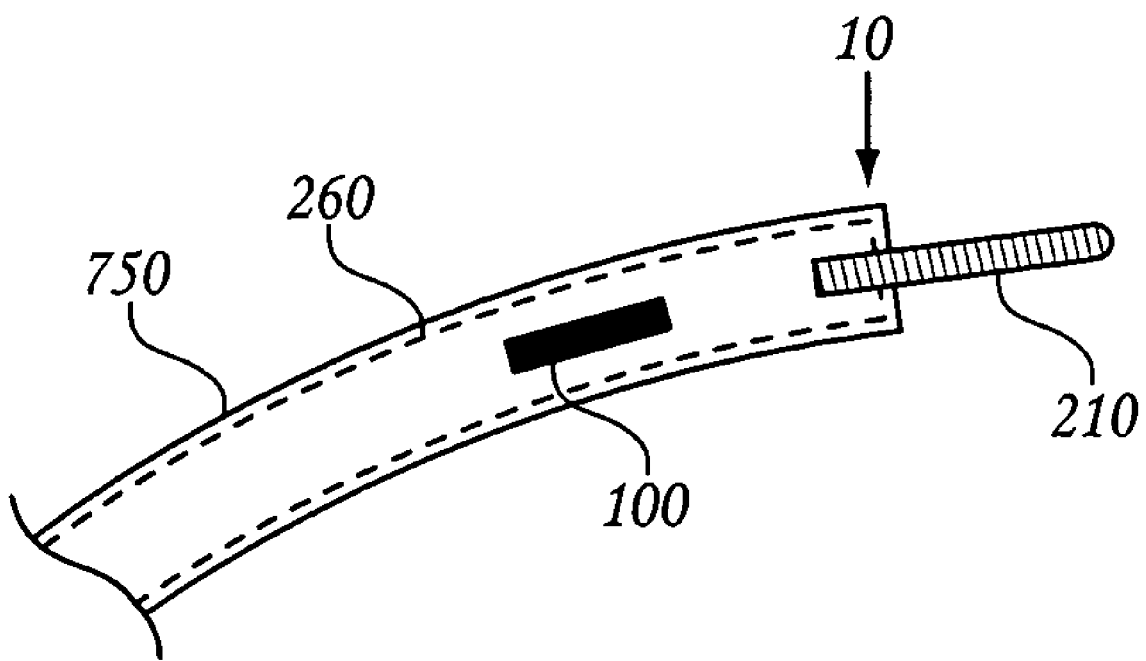
FIG. 3A depicts a type of actuator at the distal end of the elongate body.

FIG. 3a depicts another embodiment of the current invention. Elongate body 750 carries magnet or electromagnet 100. Distal end 10 contains an actuator 210 which translates as a result of force between magnet 100 and actuator 210 and which is generated by magnet 100. Switching magnet 100 between the on and off state correspondingly actuates distal actuator 210 at a given frequency and allows actuator 210 to apply force to tissues. Although depicted as a linear structure in FIG. 3a, actuator 210 can be of any shape or size, can be sharp or dull, and can be flexible, semi-flexible, or rigid. It can be composed of a polymer, metal, or ceramic.

Figure 4:
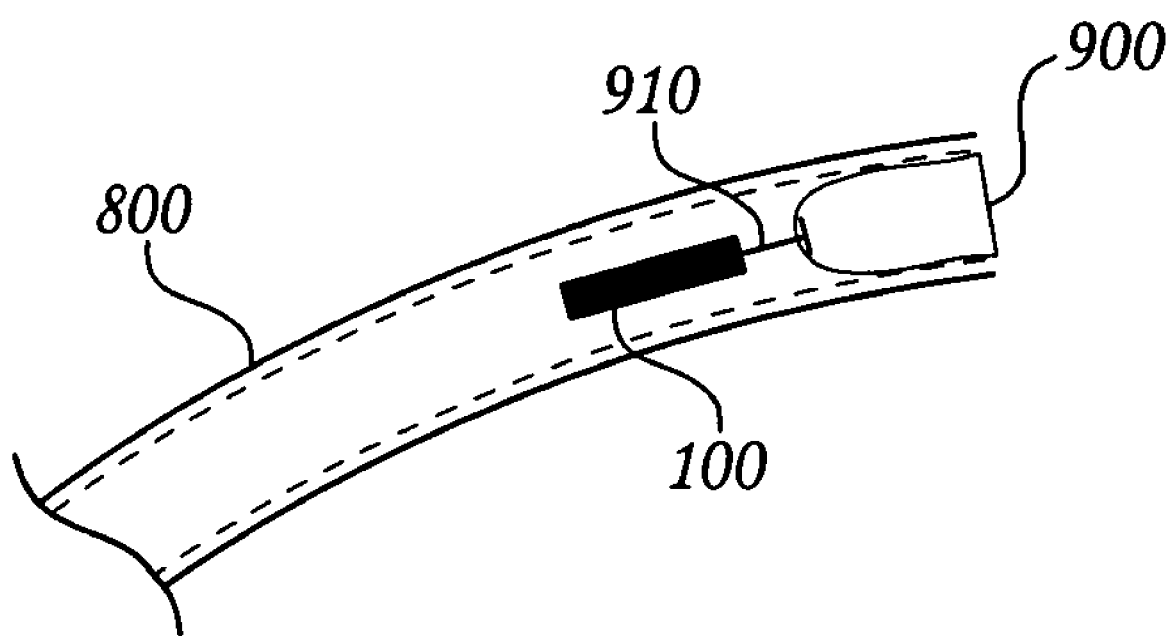
FIG. 4 depicts another example of a distal end of the elongate body.

FIG. 4 depicts another embodiment of the current invention in which magnetic actuator 100 compresses particles 900 which are contained in a compressible fluid. Actuator 910 is powered by the forces from magnet(s) 100 and the compression and acceleration of particles 900 and fluid is controllable and releasable at a pre-specified pressure.

In another embodiment, a plurality of electromagnets 100 are disposed on the elongate body 50. The bulk material properties of the elongate body are controlled by creating different forces between the magnets on the catheter. For example, the stiffness or flexibility of the catheter can be controlled by activating or deactivating one or more magnets. Depending on the strength of the force between the magnets, the flexibility of the catheter is can be varied between stiff and flexible.

Clinical Applications

The clinical applications of this invention are diverse and vast. Point of use actuation and navigation can be used in a variety of clinical settings including catheter navigation, surgical devices, thrombus removal, etc.

Methods of Manufacture

Any of the materials on the body including the magnets can be manufactured using techniques known to those skilled in the art. For example, the magnets can be glued to the body or they can be integrated into a circuit which is then glued to the body.

In another example, microfabrication techniques are used to deposit magnetic or magnetic elements on the body. In some embodiments, the magnetic elements are deposited on a board (e.g. circuit board) and then the board is fixed or glued to the catheter. The board may be composed of standard circuit board materials or the board can be manufactured from a polymer or a fabric. The microfabrication technologies available include electrodeposition (electroless and/or electroplating), vapor deposition (physical and chemical), lithography, soft-lithography, nano-imprint lithography, screen printing, and/or a variety of other methods known to those well-skilled in the arts.

The arrangement of the proximal magnetic elements is crucial to the functionality of the device. If the magnetic elements are in-line with the distal element, then torque will not be generated. If the magnetic elements are not in-line with the distal elements, the torques will be generated.

In another embodiment, the substance of the body is produced with magnetic particles (e.g. magnetic nanoparticles) inside it. For example, in the case of a catheter, the catheter material is molded with particles within the polymeric material so that the magnetic force now attracts the polymeric material.

Functionality of the Device

In some embodiments, the distal tip is vibrated by on-off cycling of the electromagnet so that the tip moves at a high speed and can disrupt tissue such as neoplastic tissue, atherosclerotic tissue, ocular tissue, etc. The tip can vibrate in a direction longitudinal to the catheter or can vibrate in a direction perpendicular to the catheter.

In other embodiments, the controllable magnets can be used to accelerate particles, such as nanoparticles, into a vascular lesion, such as an atherosclerotic plaque, or into a lesion such as a tumor. Particle acceleration can occur for at least two reasons: 1) a repelling force relative to the particle or forcing the particle out the end of the catheter at a relatively high speed; 2) the magnets on the catheter act as an actuator to directly accelerate the particles via transfer of kinetic energy or by creating a pressure on the fluid containing the particles.

What is claimed is:

1. A medical device comprising:
   a distal end adapted to be inserted into a patient;
   a proximal end adapted to interface with an operator;
   an elongate body disposed between the proximal and distal ends;
   at least one electromagnet disposed on the elongate body wherein said at least one electromagnet is disposed a first distance from the central longitudinal axis of the elongate body;
   at least one ferromagnetic or paramagnetic material disposed on or in the elongate body in a position such that the electromagnet applies a force to the ferromagnetic or paramagnetic material when current travels through the electromagnet; and,
   wherein the ferromagnetic or paramagnetic material is disposed a second distance from the central longitudinal axis of the elongate body; and
   a torque is created between the electromagnet and the material when current is passed through the electromagnet.

2. The device of claim 1 wherein the elongate body is a flexible catheter.

3. The device of claim 1 wherein the elongate body is a rigid device.

4. The device of claim 1 wherein the elongate body is a laparoscopic instrument.

5. The device of claim 1 wherein the elongate body is an endoscopic instrument.

6. The device of claim 1 wherein the ferromagnetic or paramagnetic material is mixed and entrained within the substance of the elongate body during production.

7. The device of claim 1 wherein a controller is disposed on or is associated with the elongate body; and wherein the controller modulates the amount of current transmitted to the electromagnet.

8. The device of claim 7 further comprising a user interface at the proximal end wherein the user interface translates hand movement from the user to electrical signals to the electromagnet(s).

9. The device of claim 1 further comprising a linearly translateable paramagnetic or ferromagnetic material.

10. The device of claim 9 wherein the distal tip of the elongate catheter can move in a direction perpendicular to the longitudinal axis or in the same direction of the longitudinal axis.

11. A method of treating a patient comprising:
    advancing the device of claim 1 into a patient;
    applying an electrical current to the device of claim 1 and thence to the electromagnet;
    activating the electromagnet on the device;
    inducing movement of another portion of the elongate body;
    wherein the device further comprises a pressurized chamber carrying a fluid; and activating the electromagnet results in pressurization of the fluid in the chamber.

12. The method of claim 11 further comprising: accelerating particles into a pathologic tissue of a patient.

13. The device of claim 1 wherein the elongate body comprises a plurality of electromagnets controllable to change the flexibility of the elongate body.

14. The device of claim 13 wherein said elongate body comprises a plurality of magnetic particles along its length.

15. The device of claim 1 wherein said elongate body comprises a plurality of magnetic particles along its length.

16. The device of claim 1 further adapted to accelerate particles from the distal tip.

17. A medical device comprising:
a distal end adapted to be inserted into a patient;
a proximal end adapted to interface with an operator;
an elongate body disposed between the proximal and distal ends;
at least one electromagnet disposed on the elongate body;
at least one ferromagnetic or paramagnetic material disposed on or in the elongate body in a position such that the electromagnet applies a force to the ferromagnetic or paramagnetic material when current travels through the electromagnet; and
a chamber configured to be pressurized by an actuator coupled to the electromagnet.

18. The device of claim 17 further adapted to accelerate particles from the distal tip.

* * * * *